US012766278B2

(12) United States Patent
Baker et al.

(10) Patent No.: US 12,766,278 B2
(45) Date of Patent: Oct. 20, 2026

(54) ELECTRONIC AEROSOL PROVISION SYSTEMS AND METHODS

(71) Applicant: NICOVENTURES TRADING LIMITED, London (GB)

(72) Inventors: Darryl Baker, London (GB); Ross Oldbury, London (GB)

(73) Assignee: Nicoventures Trading Limited, London (GB)

( * ) Notice: Subject to any disclaimer, the term of this patent is extended or adjusted under 35 U.S.C. 154(b) by 416 days.

(21) Appl. No.: 15/764,216

(22) PCT Filed: Sep. 8, 2016

(86) PCT No.: PCT/GB2016/052772
§ 371 (c)(1),
(2) Date: Mar. 28, 2018

(87) PCT Pub. No.: WO2017/055795
PCT Pub. Date: Apr. 6, 2017

(65) Prior Publication Data

US 2019/0053540 A1 Feb. 21, 2019

(30) Foreign Application Priority Data

Sep. 28, 2015 (GB) ..................................... 1517088

(51) Int. Cl.
*A61M 15/06* (2006.01)
*A24F 40/51* (2020.01)
(Continued)

(52) U.S. Cl.
CPC ............. *A61M 15/06* (2013.01); *A24F 40/51* (2020.01); *A24F 40/60* (2020.01); *A24F 40/65* (2020.01);
(Continued)

(58) Field of Classification Search
CPC ........ A24F 47/008; A24F 40/10; A24F 40/65; A24F 40/51; A24F 40/60; A24F 40/50;
(Continued)

(56) References Cited

U.S. PATENT DOCUMENTS 5,797,389 A * 8/1998 Ryder .................. A61M 16/12
128/200.21
6,202,642 B1 3/2001 McKinnon et al.
(Continued)

FOREIGN PATENT DOCUMENTS

AU 2016329886 B2 8/2019
CA 2906456 A1 9/2014
(Continued)

OTHER PUBLICATIONS

Translation of CN203986103U (2014).*
(Continued)

*Primary Examiner* — Tiffany T Tran
(74) *Attorney, Agent, or Firm* — Burr & Forman

(57) ABSTRACT

A system including an electronic aerosol provision device for selectively providing an aerosol to a user of the electronic aerosol provision device, a computing device configured to communicate with the electronic aerosol provision device to exchange operating data associated with the operation of the electronic aerosol provision device, and a biometric sensor configured to measure a biometric parameter of the user of the electronic aerosol provision device and to communicate with the computing device to exchange sensor data indicating a measurement of the biometric parameter. The computing device is further configured to control an aspect of its operation relating to the electronic aerosol provision device in response to the sensor data received from the biometric sensor.

15 Claims, 6 Drawing Sheets

(51) Int. Cl.

| | |
|---|---|
| ***A24F 40/60*** | (2020.01) |
| ***A24F 40/65*** | (2020.01) |
| ***A61M 11/04*** | (2006.01) |
| ***A61M 15/00*** | (2006.01) |
| *A24F 40/10* | (2020.01) |
| *A61M 16/00* | (2006.01) |

(52) U.S. Cl.

CPC ........ *A61M 11/042* (2014.02); *A61M 15/002* (2014.02); *A24F 40/10* (2020.01); *A61M 2016/0021* (2013.01); *A61M 2016/0024* (2013.01); *A61M 2205/3331* (2013.01); *A61M 2205/3368* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/3653* (2013.01); *A61M 2205/502* (2013.01); *A61M 2205/505* (2013.01); *A61M 2205/581* (2013.01); *A61M 2205/582* (2013.01); *A61M 2205/583* (2013.01); *A61M 2205/8206* (2013.01); *A61M 2205/8243* (2013.01); *A61M 2209/088* (2013.01); *A61M 2230/005* (2013.01); *A61M 2230/06* (2013.01); *A61M 2230/30* (2013.01); *A61M 2230/42* (2013.01); *A61M 2230/63* (2013.01)

(58) Field of Classification Search

CPC ........ A61M 11/042; A61M 2205/3303; A61M 15/06; A61M 15/002; A61M 2016/0021; A61M 2016/0024; A61M 2205/3331; A61M 2205/3368; A61M 2205/3553; A61M 2205/3561; A61M 2205/3569; A61M 2205/3584; A61M 2205/3592; A61M 2205/3653; A61M 2205/502; A61M 2205/505; A61M 2205/581; A61M 2205/582; A61M 2205/583; A61M 2205/8206; A61M 2205/8243; A61M 2209/088; A61M 2230/005; A61M 2230/06; A61M 2230/30; A61M 2230/42; A61M 2230/63; A61M 2205/609; A61M 2230/04; A24B 15/167; A24B 15/243

See application file for complete search history.

(56) References Cited

U.S. PATENT DOCUMENTS

| | | | | |
|---|---|---|---|---|
| 9,743,691 | B2 | 8/2017 | Minskoff et al. | |
| 2002/0017299 | A1* | 2/2002 | Hickle ................. | A61B 5/4821 128/205.25 |
| 2002/0078948 | A1* | 6/2002 | Hindle ................. | A61M 11/041 128/200.14 |
| 2008/0078385 | A1* | 4/2008 | Xiao ................. | A61M 16/1075 128/203.26 |
| 2008/0142010 | A1* | 6/2008 | Weaver ................ | A61M 11/041 128/203.26 |
| 2008/0257337 | A1* | 10/2008 | Denyer ................ | A61M 11/005 128/200.14 |
| 2009/0025714 | A1* | 1/2009 | Denyer ............. | A61M 15/0021 128/200.23 |
| 2011/0265806 | A1 | 11/2011 | Alarcon | |
| 2012/0249294 | A1* | 10/2012 | O'Connor ......... | A61M 5/14244 340/5.52 |
| 2012/0291791 | A1 | 11/2012 | Pradeep | |
| 2013/0206154 | A1 | 8/2013 | Fernando et al. | |
| 2013/0276799 | A1 | 10/2013 | Davidson | |
| 2013/0284192 | A1 | 10/2013 | Peleg | |
| 2014/0174459 | A1 | 6/2014 | Burstyn | |
| 2014/0202477 | A1 | 7/2014 | Qi et al. | |
| 2014/0246035 | A1* | 9/2014 | Minskoff .............. | A24F 47/008 131/329 |
| 2014/0275854 | A1 | 9/2014 | Venkatraman et al. | |
| 2015/0101625 | A1 | 4/2015 | Newton et al. | |
| 2015/0128976 | A1* | 5/2015 | Verleur ..................... | H02J 7/00 131/329 |
| 2015/0142387 | A1* | 5/2015 | Alarcon ............... | A61M 11/042 702/187 |
| 2015/0181945 | A1* | 7/2015 | Tremblay ................ | A24F 40/60 131/328 |
| 2015/0224268 | A1 | 8/2015 | Henry | |
| 2015/0257445 | A1 | 9/2015 | Charles | |
| 2016/0029697 | A1* | 2/2016 | Shafer ........................ | G05F 1/66 131/328 |
| 2016/0081393 | A1* | 3/2016 | Black ................... | H05B 1/0252 392/387 |
| 2016/0217565 | A1* | 7/2016 | Mozer ................... | G06T 7/0012 |
| 2016/0224779 | A1* | 8/2016 | Kitane ................ | H04L 63/0861 |
| 2016/0325058 | A1* | 11/2016 | Samson ............... | A61B 5/0022 |
| 2018/0140016 | A1* | 5/2018 | Thorens ............ | A61M 15/0068 131/329 |

FOREIGN PATENT DOCUMENTS

| | | | | | |
|---|---|---|---|---|---|
| CN | 101366626 | A | | 2/2009 | |
| CN | 101742981 | A | | 6/2010 | |
| CN | 202078307 | U | | 12/2011 | |
| CN | 103734916 | A | | 4/2014 | |
| CN | 103798960 | A | | 5/2014 | |
| CN | 103996272 | A | | 8/2014 | |
| CN | 203913385 | U | | 11/2014 | |
| CN | 203952429 | U | | 11/2014 | |
| CN | 203986103 | U | * | 12/2014 | ............. A24F 47/08 |
| CN | 104464237 | A | | 3/2015 | |
| CN | 104839891 | A | * | 8/2015 | |
| CN | 104889994 | | | 9/2015 | |
| JP | 2006081838 | | | 3/2006 | |
| JP | 6622393 | B2 | | 11/2019 | |
| KR | 20120094400 | | | 8/2012 | |
| KR | 20140090138 | A | | 7/2014 | |
| KR | 102061240 | B1 | | 12/2019 | |
| RU | 2509516 | C2 | | 3/2014 | |
| RU | 2014108052 | | | 9/2015 | |
| RU | 2697234 | C1 | | 8/2019 | |
| RU | 2737424 | C2 | | 11/2020 | |
| RU | 2762258 | C1 | | 12/2021 | |
| WO | 2008098346 | A1 | | 8/2008 | |
| WO | 2008139411 | A2 | | 11/2008 | |
| WO | WO2014150704 | A2 | | 9/2014 | |
| WO | WO2015006652 | | | 1/2015 | |
| WO | 2015076515 | A1 | | 5/2015 | |
| WO | WO2015073854 | | | 5/2015 | |
| WO | WO-2015082560 | A1 | | 6/2015 | |
| WO | 2015107552 | A1 | | 7/2015 | |
| WO | WO-2015109259 | A1 | | 7/2015 | |

OTHER PUBLICATIONS

"Separate" definition, https://www.merriam-webster.com/dictionary/separate, pp. 1-3 (Year: 2005).*

Dialog, DA14580 *Low Power Bluetooth Smart SoC*. As available at: http://www.dialog-semiconductor.com/products/bluetooth-smart/smartbond-da14580. Jan. 29, 2015, dated Jan. 29, 2015, vol. 3.1, 158 pages.

IEEE, 802.15.1 (Jun. 14, 2002) *IEEE Standard for Telecommunications and Information Exchange Between Systems—LAN/MAN—Specific Requirements—Part 15: Wireless Medium Access Control (MAC) and Physical Layer (PHY) Specifications for Wireless Personal Area Networks (WPANs)*, 2 pages.

IEEE, *802.11ah IEEE Draft Standard for Information Technology—Telecommunications and Information Exchange between Systems—Local and Metropolitan Area networks—Specific Requirements—Part 11: Wireless LAN Medium Access Control (MAC) and Physical Layer* (Feb. 2016), 2 pages.

IEEE, *IEEE Publishes the 802.11v Amendment Titled Wireless Network Management to Extend the Base IEEE 802.11™ Wireless LAN Standards* (May 13, 2011), 1 page.

(56) References Cited

OTHER PUBLICATIONS

ISO 13157-1: *2014 Information Technology—Telecommunications and information exchange between systems—NFC Security Part 1 NFC-SEC NFCIP-1 security services and protocol* (Aug. 15, 2014), 2 pages.
Bluetooth, *Bluetooth Smart Technology: Powering the Internet of things*, as available at http://www.bluetooth.com/Pages/Bluetooth-Smart.aspx (Nov. 10, 2014), 2 pages.
International Search Report and Written Opinion, Application No. PCT/GB2016/052772, mailed Dec. 21, 2016, 16 pages.
International Preliminary Report on Patentability, , Application No. PCT/GB2016/052772, mailed Jan. 26, 2018, 18 pages.
Great Britain Search Report, Application No. GB1517088.9, dated Feb. 9, 2016, 3 pages.
Written Opinion, Application No. PCT/GB2016/052772, mailed Apr. 6, 2017, 8 pages.
New Zealand First Examination Report, IP No. 740349, dated Sep. 6, 2018, 4 pages.
Russian Office Action and Search Report, Application No. 2018110804, dated Mar. 19, 2019, 2 pages.
Korean Office Action, Application No. 10-2018-7008904, dated Mar. 12, 2019, 11 pages.
Japanese Office Action, Application No. 2018-516050, dated Apr. 17, 2019, 9 pages.
New Zealand First Examination Report, IP No. 740349, dated Sep. 3, 2019, 4 pages.
Korean Notice of Allowance, Application No. 10-2018-7008904, dated Sep. 27, 2019, 3 pages.
Chinese Office Action and Search Report; Chinese Application No. 201680056365.3, mailing date Jan. 14, 2020, 28 pages.
Examination Report for New Zealand Application No. 757042 mailed Jul. 22, 2020, 5 pages.
Examination Report for New Zealand Application No. 772674, mailed on Jan. 25, 2022, 8 pages.
Office Action for Ukraine Application No. a201802902, mailed Jan. 10, 2022, 5 pages.
Reasons for Rejection received for Korean Patent Application No. 10-2022-7033858, mailed on Feb. 10, 2023, 8 pages (4 pages of English Translation and 4 pages of Official Copy).
"Office Action received for Korean Patent Application No. 10-2022-7033858, mailed on Aug. 1, 2023", 6 pages (3 pages of English Translation and 3 pages of Official Copy).
Notice of Reasons for Refusal from corresponding Japanese Application No. 2023-113742, mailed Mar. 24, 2026, all pages cited in its entirety.
First Office Action from the corresponding Chinese Application No. 202310920163.0, mailed Feb. 13, 2026, all pages cited in its entirety.

* cited by examiner

400

ELECTRONIC AEROSOL PROVISION SYSTEMS AND METHODS

PRIORITY CLAIM

The present application is a National Phase entry of PCT Application No. PCT/GB2016/052772, filed Sep. 8, 2016, which claims priority from GB Patent Application No. 1517088.9, filed Sep. 28, 2015, each of which is hereby fully incorporated herein by reference.

FIELD

The present disclosure relates to electronic aerosol provision systems such as nicotine delivery systems (e.g. electronic cigarettes and the like) and associated functionality.

BACKGROUND

Electronic aerosol provision devices such as electronic cigarettes (e-cigarettes) generally contain a reservoir of a source formulation, typically a liquid including nicotine which is sometimes referred to as an e-liquid, from which an aerosol is generated, e.g. through heat vaporization. An aerosol source for an aerosol provision device may thus comprise a heater having a heating element arranged to receive source liquid from the reservoir, for example through wicking/capillary action. While a user inhales on the device, electrical power is supplied to the heating element to vaporize source liquid in the vicinity of the heating element to generate an aerosol for inhalation by the user. The amount of power supplied to the heating element may in some cases be varied to control aspects of the aerosol generation. The devices are usually provided with one or more air inlet holes located away from a mouthpiece end of the system. When a user sucks on a mouthpiece connected to the mouthpiece end of the system, air is drawn in through the inlet holes and past the aerosol source so that vapor from the aerosol source becomes entrained in the airflow with the resulting aerosol being inhaled by the user. The practice of inhaling vaporized liquid in this manner is commonly referred to as vaping.

An e-cigarette may have an interface to support external data communications. This interface may be used, for example, to communicate with a computing device running a software application associated with the use of the e-cigarette. For example, the computing device may comprise a smart phone or tablet computer running an application ("app") provided to facilitate a user's interaction with the e-cigarette. The communications interface may be used, for example, to load control parameters and/or updated software onto the e-cigarette. Alternatively or additionally, the interface may be utilized to download data from the e-cigarette to the computing device, for example for display to a user though the user interface of an app running on the computing device. The downloaded data may, for example, represent usage parameters of the e-cigarette, fault conditions, etc. As the skilled person will be aware, many other forms of data can be exchanged between an e-cigarette and one or more external devices.

SUMMARY

According to a first aspect of certain embodiments there is provided a system comprising: an electronic aerosol provision device for selectively providing an aerosol to a user of the electronic aerosol provision device; a computing device configured to communicate with the electronic aerosol provision device to exchange operating data associated with the operation of the electronic aerosol provision device; and a biometric sensor configured to measure a biometric parameter of the user of the electronic aerosol provision device and to communicate with the computing device to exchange sensor data indicating a measurement of the biometric parameter; and wherein the computing device is configured to control an aspect of its operation relating to the electronic aerosol provision device in response to the sensor data received from the biometric sensor.

According to another aspect of certain embodiments there is provided the electronic aerosol provision device of the first aspect.

According to another aspect of certain embodiments there is provided a method of operating a system comprising an electronic aerosol provision device, a computing device configured to communicate with the electronic aerosol provision device to exchange operating data associated with the operation of the electronic aerosol provision device, and a biometric sensor configured to measure a biometric parameter of a user of the electronic aerosol provision device and to communicate with the computing device to exchange sensor data indicating a measurement of the biometric parameter; wherein the method comprises: the biometric sensor measuring a biometric parameter of a user of the electronic aerosol provision device and communicating sensor data indicating a measurement of the biometric parameter to the computing device; and the computing device controlling an aspect of its operation relating to the electronic aerosol provision device in response to the sensor data received from the biometric sensor.

According to another aspect of certain embodiments there is provided a computing device configured to communicate with an electronic aerosol provision device to exchange operating data associated with the operation of the electronic aerosol provision device and to communicate with a biometric sensor to receive sensor data from the biometric sensor indicating a measurement of a biometric parameter of a user of the electronic aerosol provision device, wherein the computing device is further configured to control an aspect of its operation relating to the electronic aerosol provision device in response to the sensor data received from the biometric sensor.

According to another aspect of certain embodiments there is provided a method of operating a computing device configured to communicate with an electronic aerosol provision device to exchange operating data associated with the operation of the electronic aerosol provision device, the method comprising communicating with a biometric sensor to receive sensor data from the biometric sensor indicating a measurement of a biometric parameter of a user of the electronic aerosol provision device and controlling an aspect of the computing device's operation relating to the electronic aerosol provision device in response to the sensor data received from the biometric sensor.

According to another aspect of certain embodiments there is provided a computer program product comprising machine readable instructions which when executed on a computing device configure the computing device to communicate with an electronic aerosol provision device to exchange operating data associated with the operation of the electronic aerosol provision device, to communicate with a biometric sensor to receive sensor data from the biometric sensor indicating a measurement of a biometric parameter of a user of the electronic aerosol provision device, and to control an aspect of the computing device's operation relating to the electronic aerosol provision device in response to the sensor data received from the biometric sensor.

According to another aspect of certain embodiments there is provided a system comprising: electronic aerosol provision means for selectively providing an aerosol to a user of the electronic aerosol provision means; computing means for communicating with the electronic aerosol provision means to exchange operating data associated with the operation of the electronic aerosol provision means; and biometric sensor means for measuring a biometric parameter of the user of the electronic aerosol provision means and communicating with the computing means to exchange sensor data indicating a measurement of the biometric parameter; and wherein the computing means controls an aspect of its operation relating to the electronic aerosol provision means in response to the sensor data received from the biometric means.

It will be appreciated that features and aspects of the disclosure described above in relation to the first and other aspects of the disclosure are equally applicable to, and may be combined with, embodiments of the disclosure according to other aspects of the disclosure as appropriate, and not just in the specific combinations described above.

Further respective aspects and features of the disclosure are defined in the appended claims.

BRIEF DESCRIPTION OF THE DRAWINGS

Embodiments of the present disclosure will now be described by way of example with reference to the accompanying drawings, in which.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to an aerosol provision device, such as an e-cigarette. Throughout the following description the term "e-cigarette" is used; however, this term may be used interchangeably with electronic vapor provision device, aerosol delivery device, and other similar terminology.

Figure 1:
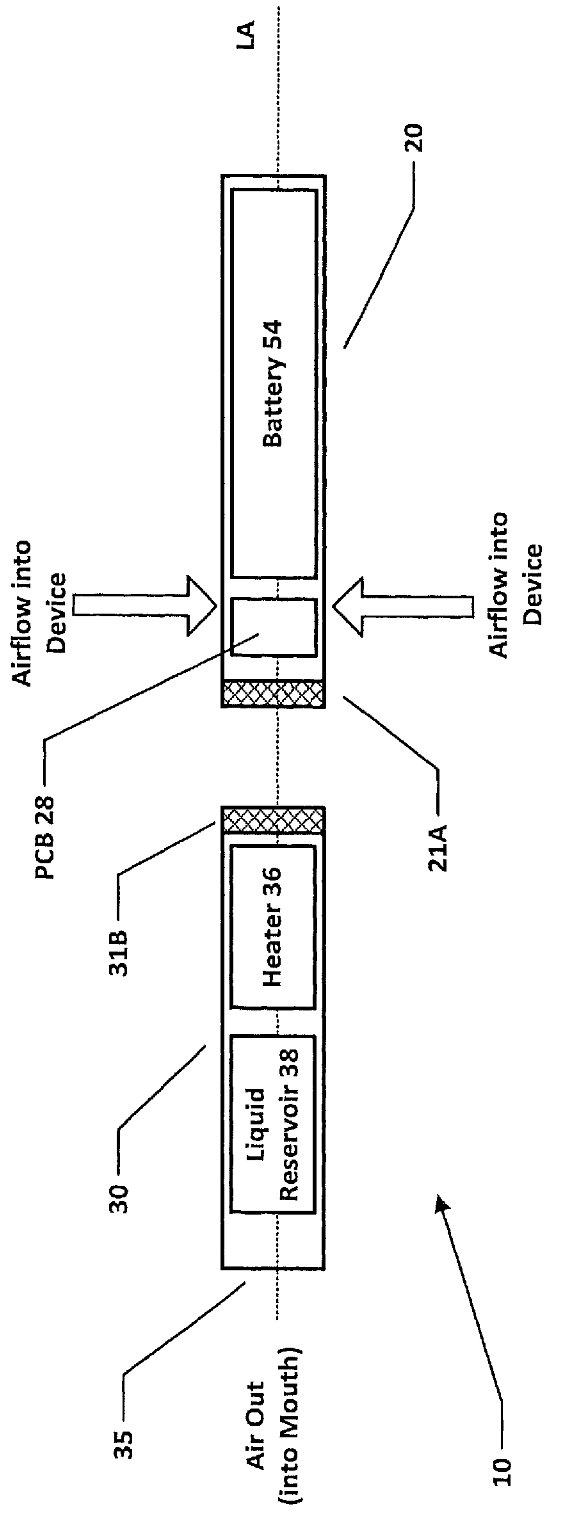
FIG. 1 is a schematic (exploded) diagram of an e-cigarette in accordance with some embodiments of the disclosure.

FIG. 1 is a schematic (exploded) diagram of an e-cigarette 10 in accordance with some embodiments of the disclosure (not to scale). The e-cigarette 10 comprises a body or control unit 20 and a cartomizer 30. The cartomizer 30 includes a reservoir 38 of liquid, typically including a liquid and nicotine and/or flavoring, a heater 36, and a mouthpiece 35. The e-cigarette 10 in this example has a longitudinal or cylindrical axis which extends along a center-line of the e-cigarette 10 from the mouthpiece 35 at one end of the cartomizer 30 to an opposing end of the control unit 20 (usually referred to as the tip end). This longitudinal axis is indicated in FIG. 1 by the dashed line denoted LA.

The liquid reservoir 38 in the cartomizer 30 may hold the (e-)liquid directly in free liquid form, or may utilize some absorbing structure, such as a foam matrix or cotton material, etc., as a retainer for the liquid. The liquid is then fed from the reservoir 38 to be delivered to a vaporizer comprising the heater 36. For example, liquid may flow via capillary action from the reservoir 38 to the heater 36 via a wick (not shown in FIG. 1).

Although the examples described herein primarily focus on electronic smoking devices employing an aerosol forming substrate in the form of a liquid, it will be appreciated that the same principles can be applied in respect of electronic smoking devices employing aerosol forming substrate which are provided in solid form, for example comprising a plant material/plant derivative material. Note that devices containing a solid aerosol forming substrate do not typically employ a wick to transport the formulation to the heater, but rather provide a suitable arrangement of the heater in relation to the material to provide suitable heating and vaporization.

The control unit 20 includes a re-chargeable cell or battery 54 to provide power to the e-cigarette 10 (referred to hereinafter as a battery) and a printed circuit board (PCB) 28 and/or other electronics for generally controlling the e-cigarette 10.

The control unit 20 and the cartomizer 30 are in this example detachable from one another, as shown in FIG. 1, but are joined together when the device 10 is in use, for example, by a screw or bayonet fitting. The connectors on the cartomizer 30 and the control unit 20 are indicated schematically in FIG. 1 as 31B and 21A respectively. This connection between the control unit 20 and cartomizer 30 provides for mechanical and electrical connectivity between the two.

When the control unit 20 is detached from the cartomizer 30, the electrical connection 21A on the control unit 20 that is used to connect to the cartomizer 30 may also serve as a socket for connecting a charging device (not shown). The other end of this charging device can be plugged into a USB socket to re-charge the battery 54 in the control unit 20 of the e-cigarette 10. In other implementations, the e-cigarette 10 may be provided (for example) with a cable for direct connection between the electrical connection 21A and a USB socket.

The control unit 20 is provided with one or more holes for air inlet adjacent to PCB 28. These holes connect to an air passage through the control unit 20 to an air passage provided through the connector 21A. This then links to an air path through the cartomizer 30 to the mouthpiece 35. Note that the heater 36 and the liquid reservoir 38 are configured to provide an air channel between the connector 31B and the mouthpiece 35. This air channel may flow through the center of the cartomizer 30, with the liquid reservoir 38 confined to an annular region around this central path. Alternatively (or additionally) the airflow channel may lie between the liquid reservoir 38 and an outer housing of the cartomizer 30.

When a user inhales through the mouthpiece 35, air is drawn into or past the control unit 20 through the one or more air inlet holes. This airflow (or the associated change in pressure) is detected by a sensor, e.g. a pressure sensor, which in turn activates the heater 36 to vaporize the nicotine liquid fed from the reservoir 38. The airflow passes into the vaporizer, where the airflow combines with the vapor from the heated aerosol forming substrate, in this case liquid from the liquid reservoir 38. This combination of airflow and source formulation vapor (in effect, an aerosol) then passes through the cartomizer 30 and out of the mouthpiece 35 to be inhaled/vaped by a user. The cartomizer 30 may be detached from the control unit 20 and disposed of when the supply of liquid is exhausted and replaced with another cartomizer 30.

It will be appreciated that the e-cigarette 10 shown in FIG. 1 is presented by way of example only, and many other implementations may be adopted. For example, in some implementations, the cartomizer 30 is split into a cartridge containing the liquid reservoir 38 and a separate vaporizer portion containing the heater 36. In this configuration, the cartridge may be disposed of after the liquid in reservoir 38 has been exhausted, but the separate vaporizer portion containing the heater 36 is retained. Alternatively, an e-cigarette 10 may be provided with a cartomizer 30 as shown in FIG. 1, or else constructed as a one-piece (unitary) device, but the liquid reservoir 38 is in the form of a (user-) replaceable cartridge and/or the liquid reservoir 38 may be user-refillable. Further possible variations are that the heater 36 may be located at the opposite end of the cartomizer 30 from that shown in FIG. 1, i.e. between the liquid reservoir 38 and the mouthpiece 35, or else the heater 36 is located along a central axis LA of the cartomizer 30, and the liquid reservoir 38 is in the form of an annular structure which is radially outside the heater 35.

The skilled person will also be aware of a number of possible variations for the control unit 20. For example, airflow may enter the control unit 20 at the tip end, i.e. the opposite end to connector 21A, in addition to or instead of the airflow adjacent to PCB 28. In this case the airflow would typically be drawn towards the cartomizer 30 along a passage between the battery 54 and the outer wall of the control unit 20. Similarly, the control unit 20 may comprise a PCB located on or near the tip end, e.g. between the battery and the tip end. Such a PCB may be provided in addition to or instead of PCB 28.

Furthermore, an e-cigarette 10 may support charging at the tip end, or via a socket elsewhere on the device, in addition to or in place of charging at the connection point between the cartomizer 30 and the control unit 20. (It will be appreciated that some e-cigarettes are provided as essentially integrated units, in which case a user is unable to disconnect the cartomizer from the control unit.) Other e-cigarettes may also support wireless (induction) charging, in addition to (or instead of) wired charging.

The above discussion of potential variations to the e-cigarette 10 shown in FIG. 1 is by way of example. The skilled person will aware of further potential variations (and combination of variations) for the e-cigarette 10.

Figure 2:
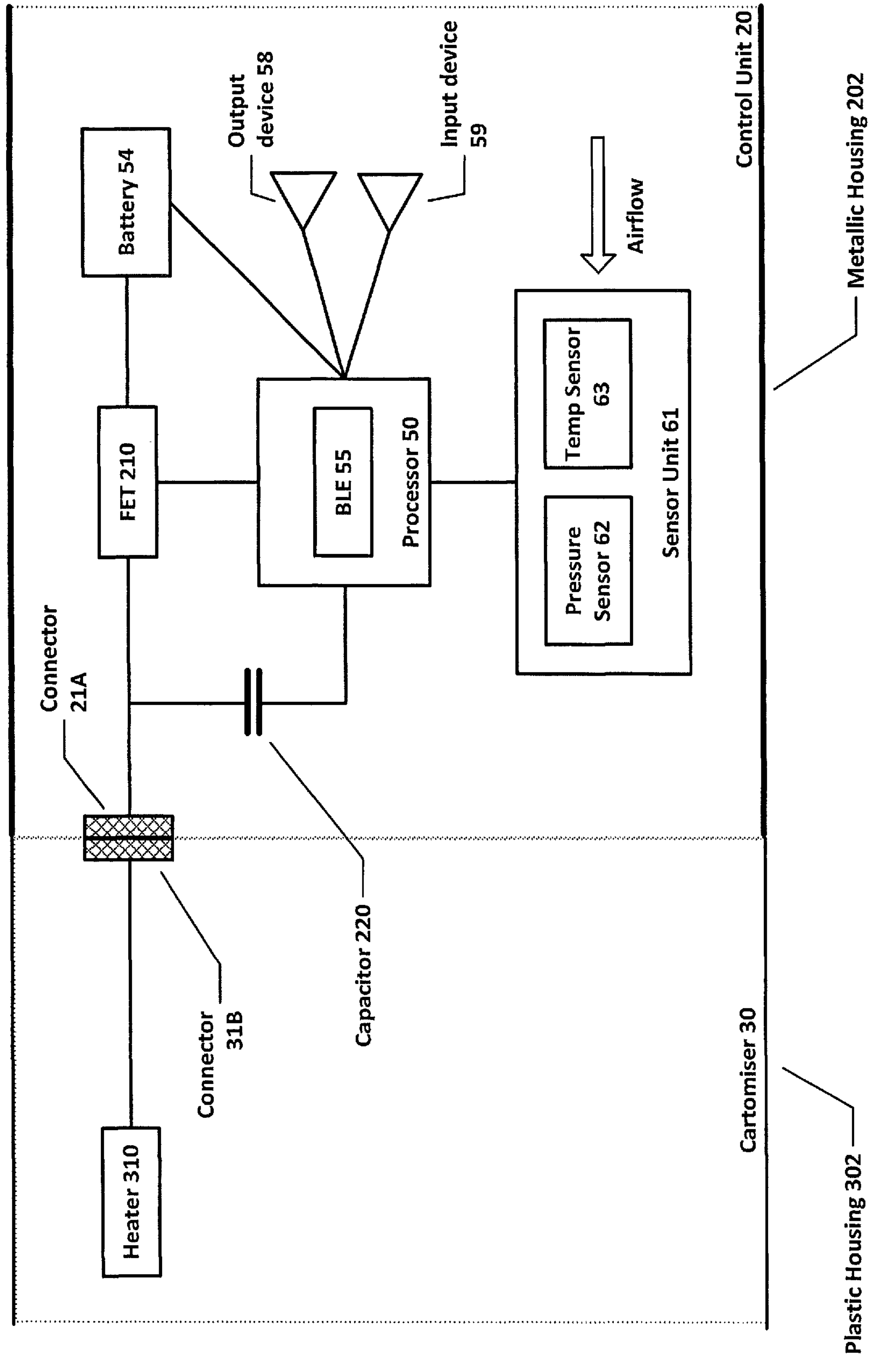
FIG. 2 is a schematic diagram of the main electrical/electronic components of the e-cigarette of FIG. 1 in accordance with some embodiments of the disclosure.

FIG. 2 is a schematic diagram of the main functional components of the e-cigarette 10 of FIG. 1 in accordance with some embodiments of the disclosure. It will be recognized that FIG. 2 is primarily concerned with electrical connectivity and functionality and is not intended to indicate the physical sizing of the different components, nor details of their physical placement within the control unit 20 or cartomizer 30. In addition, it will be appreciated that at least some of the components shown in FIG. 2 located within the control unit 20 may be mounted on the circuit board 28. Alternatively, one or more of such components may instead be accommodated in the control unit 20 to operate in conjunction with the circuit board 28, but not physically mounted on the circuit board 28 itself. For example, these components may be located on one or more additional circuit boards, or they may be separately located (such as battery 54). More generally, it will also be appreciated that whereas various elements of the electronic cigarette 10 are schematically represented in FIG. 2 as separate elements for ease of explanation, in some example implementations the functionality of one or more of these units may be provided by a single element, for example a suitably programmed processor element.

As shown in FIG. 2, and discussed above, the cartomizer 30 contains heater 310 which receives power through connector 31B. The control unit 20 includes an electrical socket or connector 21A for connecting to the corresponding connector 31B of the cartomizer 30 (or potentially to a USB charging device). This then provides electrical connectivity between the control unit 20 and the cartomizer 30.

The control unit 20 further includes a sensor unit 61, which is located in or adjacent to the air path through the control unit 20 from the air inlet(s) to the air outlet (to the cartomizer 30 through the connector 21A). The sensor unit 61 contains a pressure sensor 62 and temperature sensor 63 (also in or adjacent to this air path). The control unit 20 further includes a capacitor 220, a processor 50, a field effect transistor (FET) switch 210, a battery 54, and input and output devices 59, 58.

The operations of the processor 50 and other electronic components, such as the pressure sensor 62, are generally controlled at least in part by software programs running on the processor (or other components). Such software programs may be stored in non-volatile memory, such as ROM, which can be integrated into the processor 50 itself, or provided as a separate component. The processor 50 may access the ROM to load and execute individual software programs as and when required. The processor 50 also contains appropriate communications facilities, e.g. pins or pads (plus corresponding control software), for communicating as appropriate with other devices in the control unit 20, such as the pressure sensor 62.

The output device(s) 58 may provide visible, audio and/or haptic output. For example, the output device(s) may include a speaker 58, a vibrator, and/or one or more lights. The lights are typically provided in the form of one or more light emitting diodes (LEDs), which may be the same or different colors (or multi-colored). In the case of multi-colored LEDs, different colors are obtained by switching different colored, e.g. red, green or blue, LEDs on, optionally at different relative brightness to give corresponding relative variations in color.

The output from the output device may be used to signal to the user various conditions or states within the e-cigarette 10, such as a low battery warning. Different output signals may be used for signaling different states or conditions. For example, if the output device 58 is an audio speaker, different states or conditions may be represented by tones or beeps of different pitch and/or duration, and/or by providing multiple such beeps or tones. Alternatively, if the output device 58 includes one or more lights, different states or conditions may be represented by using different colors, pulses of light or continuous illumination, different pulse durations, and so on. For example, one indicator light might be utilized to show a low battery warning, while another indicator light might be used to indicate that the liquid reservoir 58 is nearly depleted. It will be appreciated that a given e-cigarette 10 may include output devices to support multiple different output modes (audio, visual etc.).

The input device(s) 59 may be provided in various forms. For example, an input device (or devices) 59 may be implemented as buttons on the outside of the e-cigarette 10—e.g. as mechanical, electrical or capacitive (touch) sensors. Some devices may support blowing into or sucking on the e-cigarette 10 as an input mechanism (such blowing/sucking may be detected by pressure sensor 62, which would then be also acting as a form of input device 59), and/or connecting/disconnecting the cartomizer 30 and control unit 20 as another form of input mechanism. Again, it will be appreciated that a given e-cigarette 10 may include input devices 59 to support multiple different input modes.

As noted above, the e-cigarette 10 provides an air path from the air inlet through the e-cigarette 10, past the pressure sensor 62 (or past an opening to an air channel leading to the pressure sensor) and the heater 310 in the cartomizer 30 to the mouthpiece 35. Thus when a user inhales on the mouthpiece 35 of the e-cigarette 10, the processor 50 detects such inhalation based on information from the pressure sensor 62. In response to such a detection, the CPU supplies power from the battery 54 to the heater 310, which thereby heats and vaporizes the nicotine from the liquid reservoir 38 for inhalation by the user.

In the particular implementation shown in FIG. 2, a FET 210 is connected between the battery 54 and the connector 21A. This FET 210 acts as a switch. The processor 50 is connected to the gate of the FET to operate the switch, thereby allowing the processor 50 to switch on and off the flow of power from the battery 54 to heater 310 according to the status of the detected airflow. It will be appreciated that the heater current can be relatively large, for example, in the range 1-5 amps, and hence the FET 210 should be implemented to support such current control (likewise for any other form of switch that might be used in place of FET 210).

In order to provide more fine-grained control of the amount of power flowing from the battery 54 to the heater 310, a pulse-width modulation (PWM) scheme may be adopted. A PWM scheme may be based on a repetition period of say 1 ms. Within each such period, the switch 210 is turned on for a proportion of the period, and turned off for the remaining proportion of the period. This is parameterized by a duty cycle, whereby a duty cycle of 0 indicates that the switch is off for all of each period (i.e. in effect, permanently off), a duty cycle of 0.33 indicates that the switch is on for a third of each period, a duty cycle of 0.66 indicates that the switch is on for two-thirds of each period, and a duty cycle of 1 indicates that the FET 210 is on for all of each period (i.e. in effect, permanently on). It will be appreciated that these are only given as example settings for the duty cycle, and intermediate values can be used as appropriate.

The use of PWM provides an effective power to the heater 310 which is given by the nominal available power (based on the battery output voltage and the heater resistance) multiplied by the duty cycle. The processor 50 may, for example, utilize a duty cycle of 1 (i.e. full power) at the start of an inhalation to initially raise the heater 310 to its desired operating temperature as quickly as possible. Once this desired operating temperature has been achieved, the processor 50 may then reduce the duty cycle to some suitable value in order to supply the heater 310 with the desired operating power.

As shown in FIG. 2, the processor 50 includes a communications interface 55 for wireless communications, in particular in this example, support for Bluetooth® Low Energy (BLE) communications.

Optionally the heater 310 may be utilized as an antenna for use by the communications interface 55 for transmitting and receiving the wireless communications. One motivation for this is that the control unit 20 may have a metal housing 202, whereas the cartomizer portion 30 may have a plastic housing 302 (reflecting the fact that the cartomizer 30 is disposable, whereas the control unit 20 is retained and therefore may benefit from being more durable). The metal housing 202 acts as a screen or barrier which can affect the operation of an antenna located within the control unit 20 itself. However, utilizing the heater 310 as the antenna for the wireless communications can help to avoid this metal screening because of the plastic housing 302 of the cartomizer 30, but without adding additional components or complexity (or cost) to the cartomizer. Alternatively a separate antenna may be provided (not shown), or a portion of the metal housing 202 may be used.

If the heater is used as an antenna then as shown in FIG. 2, the processor 50, more particularly the communications interface 55, may be coupled to the power line from the battery 54 to the heater 310 (via connector 31B) by a capacitor 220. This capacitive coupling occurs downstream of the switch 210, since the wireless communications may operate when the heater 310 is not powered for heating (as discussed in more detail below). It will be appreciated that capacitor 220 helps prevent the power supply from the battery 54 to the heater 310 being diverted back to the processor 50.

Note that the capacitive coupling may be implemented using a more complex LC (inductor-capacitor) network, which can also provide impedance matching with the output of the communications interface 55. (As known to the person skilled in the art, this impedance matching can help support proper transfer of signals between the communications interface 55 and the heater 310 acting as the antenna, rather than having such signals reflected back along the connection.)

In some implementations, the processor 50 and communications interface are implemented using a Dialog DA14580 chip from Dialog Semiconductor PLC, based in Reading, United Kingdom. Further information (and a data sheet) for this chip is available, for example, at www.dialog-semiconductor.com.

Figure 3:
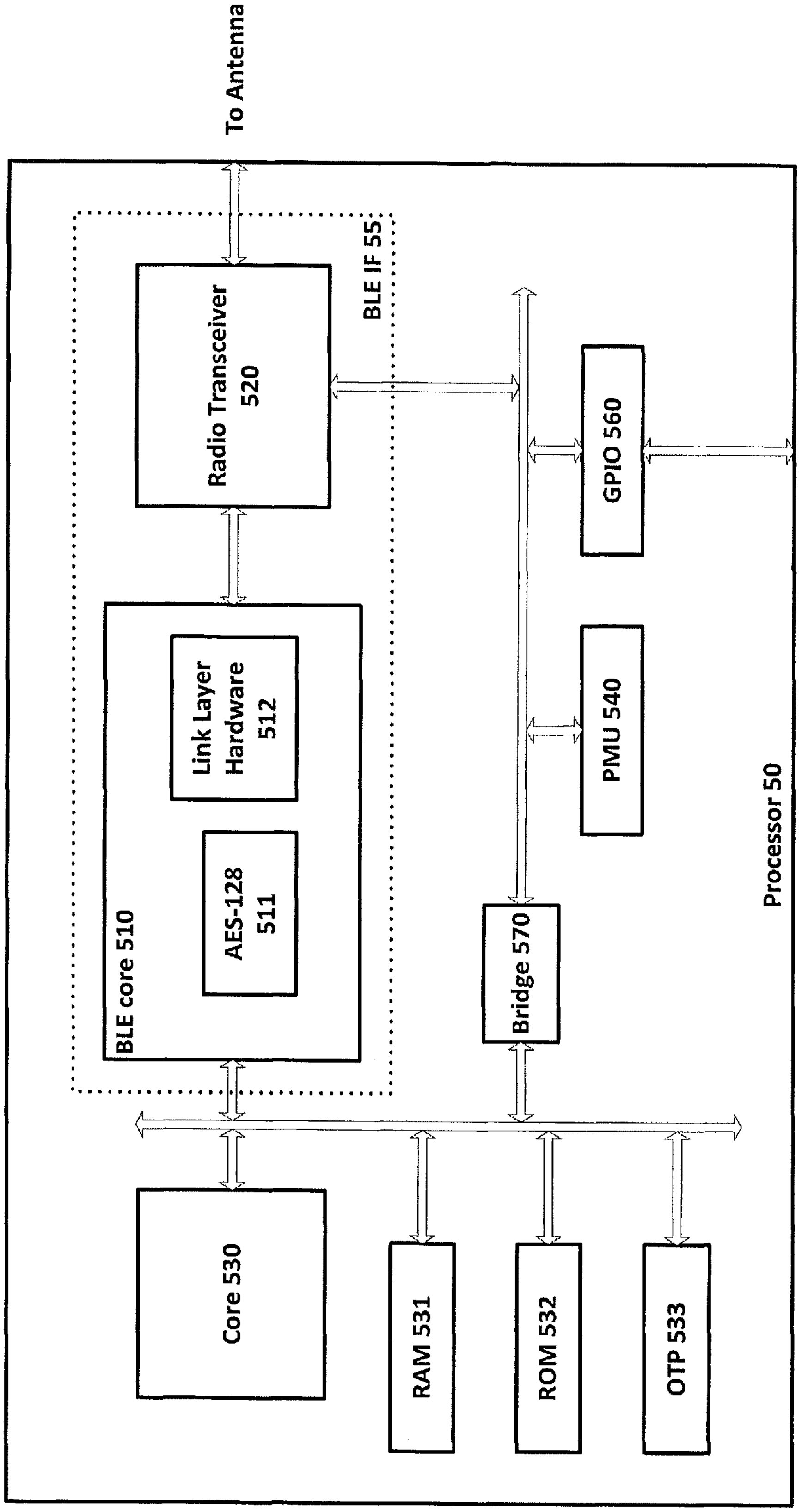
FIG. 3 is a simplified schematic diagram of the processor of the e-cigarette of FIG. 1 in accordance with some embodiments of the disclosure.

FIG. 3 presents a high-level and simplified overview of this chip 50, including the communications interface 55 for supporting Bluetooth® Low Energy. This interface 55 includes in particular a radio transceiver 520 for performing signal modulation and demodulation, etc., link layer hardware 512, and an advanced encryption facility (128 bits) 511. The output from the radio transceiver 520 is connected to the antenna (for example, to the heater 310 acting as the antenna via capacitive coupling 220 and connectors 21A and 31B).

The processor 50 further includes a general processing core 530, RAM 531, ROM 532, a one-time programming (OTP) unit 533, a general purpose I/O system 560 (for communicating with other components on the PCB 28), a power management unit 540 and a bridge 570 for connecting two buses. Software instructions stored in the ROM 532 and/or OTP unit 533 may be loaded into RAM 531 (and/or into memory provided as part of core 530) for execution by one or more processing units within core 530. These software instructions cause the processor 50 to implement functionality as described herein, such as interfacing with the sensor unit 61 and controlling the heater accordingly. Note that although the device shown in FIG. 3 acts as both a communications interface 55 and also as a general controller for the electronic vapor provision device 10, in other embodiments these two functions may be split between two or more different devices (chips)—e.g. one chip may serve as the communications interface 55, and another chip as the general controller for the electronic vapor provision device 10.

In some implementations, the processor 50 may be configured to prevent wireless communications when the heater 310 is being used for vaporizing liquid from reservoir 38. For example, wireless communications may be suspended, terminated or prevented from starting when switch 210 is switched on. Conversely, if wireless communications are ongoing, then activation of the heater 310 may be prevented—e.g. by disregarding a detection of airflow from the sensor unit 61, and/or by not operating switch 210 to turn on power to the heater 310 while the wireless communications are progressing.

One reason for preventing the simultaneous operation of heater 310 for both heating and wireless communications in some implementations is to help avoid potential interference from the PWM control of the heater. This PWM control has its own frequency (based on the repetition frequency of the pulses), albeit typically much lower than the frequency used for the wireless communications, and the two could potentially interfere with one another. In some situations, such interference may not, in practice, cause any problems, and simultaneous operation of heater 310 for both heating and wireless communications may be allowed (if so desired). This may be facilitated, for example, by techniques such as the appropriate selection of signal strengths and/or PWM frequency, the provision of suitable filtering, etc.

Figure 4:
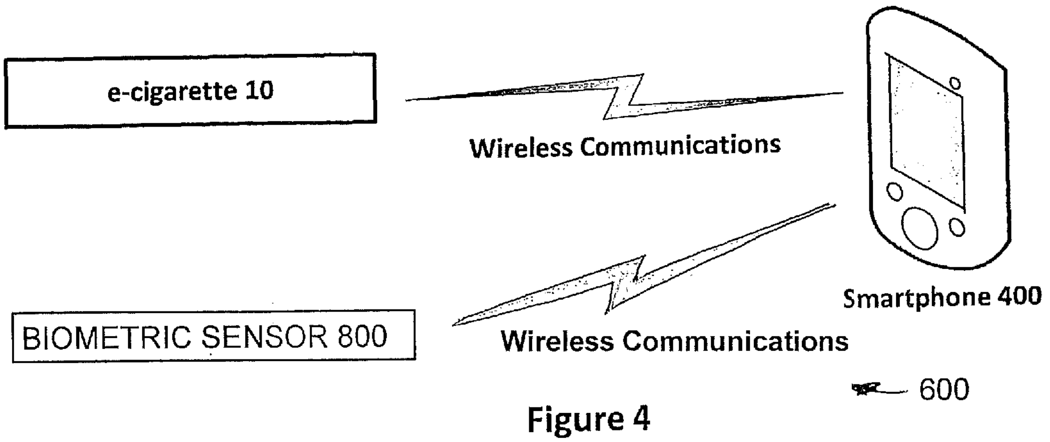
FIG. 4 is a schematic diagram of a system supporting wireless communications between an e-cigarette, a mobile communication device and a biometric sensor.

FIG. 4 is a schematic diagram showing a system 600 supporting Bluetooth® Low Energy communications between an e-cigarette 10, a smart phone 400 and a biometric sensor 800 arranged to measure a biometric parameter, such as a heart rate, of a user of the e-cigarette 10. Although this particular example is presented in the context of a smart phone running an application for supporting user interaction with the e-cigarette 10 and biometric sensor 800, it will be appreciated other computing devices with suitable communications functionality could equally be used, for example, a tablet, laptop, smartwatch, smart TV, etc. In accordance with certain example embodiments of the disclosure, and as discussed in more further below, the smart phone 400 also supports wireless communications with the biometric sensor 800 for obtaining information regarding measurements of a biometric parameter for a user of the e-cigarette.

Communications between the e-cigarette 10 and the smart phone/computing device 400 can be used to support a wide range of functions, for example, to upgrade firmware on the e-cigarette 10, to retrieve usage and/or diagnostic data from the e-cigarette 10, to reset or unlock the e-cigarette 10, to control settings on the e-cigarette 10, etc.

In general terms, when the e-cigarette 10 is switched on, such as by using input device 59, or possibly by joining the cartomizer 30 to the control unit 20, it starts to advertise for Bluetooth® Low Energy communication. If this outgoing communication is received by smart phone 400, then the smart phone 400 requests a connection to the e-cigarette 10. The e-cigarette may notify this request to a user via output device 58, and wait for the user to accept or reject the request via input device 59. Assuming the request is accepted, the e-cigarette 10 is able to communicate further with the smart phone 400. Note that the e-cigarette 10 may remember the identity of smart phone 400 and be able to accept future connection requests automatically from that smart phone 400. Once the connection has been established, the smart phone 400 and the e-cigarette 10 operate in a client-server mode, with the smart phone 400 operating as a client that initiates and sends requests to the e-cigarette 10 which therefore operates as a server (and responds to the requests as appropriate).

A Bluetooth® Low Energy link (also known as Bluetooth Smart®) implements the IEEE 802.15.1 standard, and operates at a frequency of 2.4-2.5 GHz, corresponding to a wavelength of about 12 cm, with data rates of up to 1 Mbit/s. The set-up time for a connection is less than 6 ms, and the average power consumption can be very low—of the order 1 mW or less. A Bluetooth® Low Energy link may extend up to some 50 m. However, for the situation shown in FIG. 4, the e-cigarette 10 and the smart phone 400 will typically belong to the same person, and will therefore be in much closer proximity to one another—e.g. 1 m. Further information about Bluetooth® Low Energy can be found in the relevant operating standard documents and also, for example, at www.bluetooth.com.

It will be appreciated that e-cigarette 10 may support other communications protocols for communication with smart phone 400 (or any other appropriate device). Such other communications protocols may be instead of, or in addition to, Bluetooth® Low Energy. Examples of such other communications protocols include Bluetooth® (not the low energy variant), see for example, www.bluetooth.com, near field communications (NFC), as per ISO 13157, and WiFi®. NFC communications operate at much lower wavelengths than Bluetooth (13.56 MHz) and generally have a much shorter range—say <0.2 m. However, this short range is still compatible with most usage scenarios such as shown in FIG. 4. Meanwhile, low-power WiFi® communications, such as IEEE802.11ah, IEEE802.11v, or similar, may be employed between the e-cigarette 10 and a remote device. In each case, a suitable communications chipset may be included on PCB 28, either as part of the processor 50 or as a separate component. The skilled person will be aware of other wireless communication protocols that may be employed in e-cigarette 10.

Thus, and as already mentioned above, the e-cigarette 10 can communicate with a mobile communication device 400, for example by pairing the devices using the Bluetooth® low energy protocol so that it is possible to provide additional functionality for a user of the electronic cigarette 10 and the smart phone 400, by providing suitable software instructions (for example in the form of an app) to run on the smart phone 400.

Figure 5:
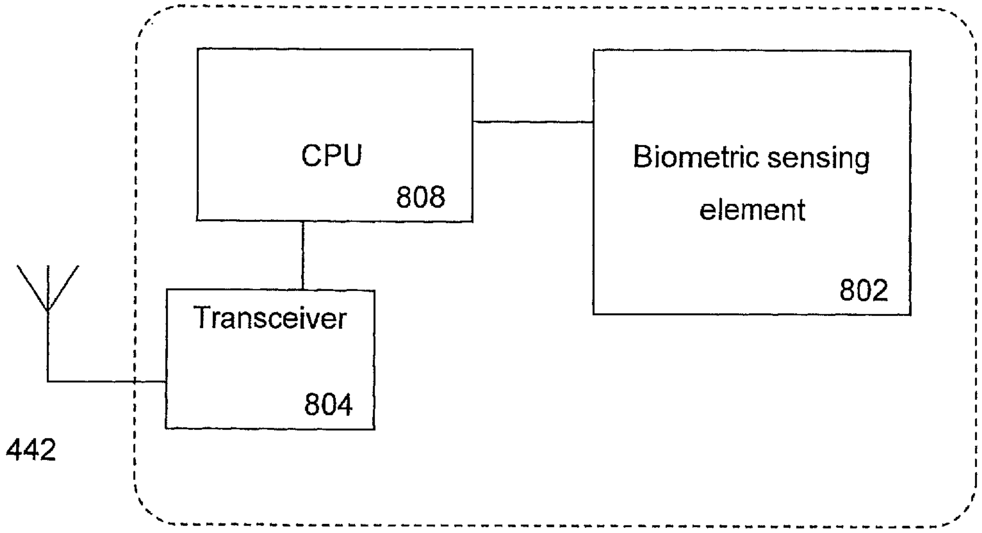
FIG. 5 is a schematic diagram showing further details of the biometric sensor of FIG. 4.

FIG. 5 is a schematic diagram of the main functional components of the biometric sensor 800 of FIG. 4. In this example it is assumed the biometric sensor 800 is a heart rate monitor configured to measure the heart rate of a user. In other examples the biometric sensor 800 may instead, or additionally, comprise a blood pressure sensor for measuring a user's blood pressure, a breathing rate sensor for measuring a user's breathing rate, and/or and/or a user activity sensor for measuring an aspect of a user's activity. The biometric sensor 800 may be based on conventional biometric sensor hardware that may be configured to operate in a system providing the functionality described herein. It will be appreciated the biometric sensor 800, and indeed the elements represented in all the other figures described herein, will in practice comprise further components (e.g. a power supply) which are not specifically represented in the figures or discussed herein in the interest of brevity. Thus, the biometric sensor 800 comprises a biometric sensing element 802, a central processing unit (CPU) 808, a transceiver unit 804 and an antenna 806. The CPU 808 is configured to communicate with the biometric sensing element 802 and transceiver 804 over a communications bus in accordance with conventional techniques.

The biometric sensing element 802 is configured to measure a biometric parameter of a user, i.e. in this example a heart rate, and it may do this in accordance with conventional techniques. For example, the biometric sensor 800 may comprise a watch-like device to be worn on a user's wrist with heart rate measuring functionality. In this respect the biometric sensor 800 may adopt similar techniques to those used in conventional heart rate monitors supporting wireless communications functionality. The CPU 808 is configured to receive measurements of the user's heart rate from the biometric sensing element 802 and to control the transceiver unit 804 to wirelessly transmit an indication of the biometric measurement(s) to the smart phone 400 using the antenna 806. In this respect the communications between the biometric sensor 800 and the smart phone 400 may be configured and operate in accordance with conventional wireless communications techniques, for example in accordance with one or more of the many established protocols for wireless communications, such as Bluetooth® (standard or low-energy variants), near field communication and Wi-Fi® as described previously, and also phone based communication such as 2G, 3G and/or 4G.

Thus, and as for the e-cigarette 10, the biometric sensor 800 can communicate with the mobile communication device 400, for example by pairing using the Bluetooth® low energy protocol, so that it is possible to provide the system with additional functionality that takes account of biometric measurements for a user of the electronic cigarette 10 and the smart phone 400, by providing suitable software instructions (for example in the form of an app) to run on the smart phone 400.

Figure 6:
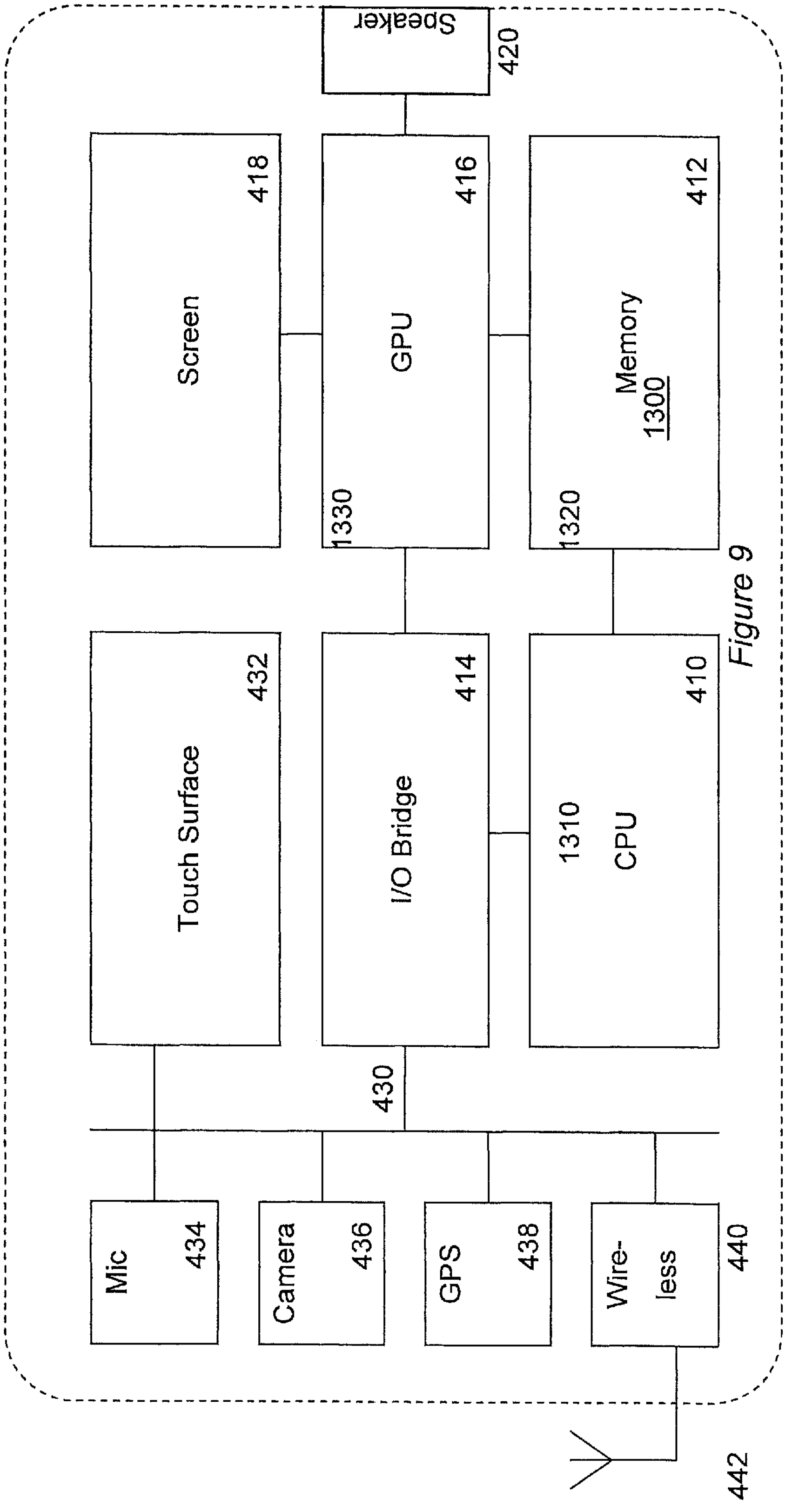
FIG. 6 is a schematic diagram showing further details of the mobile communication device of FIG. 4.

FIG. 6 is a schematic diagram of the main functional components of the smart phone 400 of FIG. 4 in accordance with some embodiments of the disclosure. It will be recognized that as for the other figures described herein, FIG. 6 is not intended to indicate the physical sizing of the different components, nor details of their relative physical placements. The smart phone 400 may comprise conventional smart phone hardware which is configured to operate to provide the functionality described herein by running a suitably programmed software application (app).

Thus, the smart phone 400 comprises a central processing unit (CPU) (410) which may communicate with components of the smart phone either through direct connections or via an I/O bridge 414 and/or a bus 430 as applicable.

In the example shown in FIG. 6, the CPU 410 communicates directly with a memory 412, which may comprise a persistent memory such as for example Flash® memory for storing an operating system and applications (apps), and volatile memory such as RAM for holding data currently in use by the CPU 410. Typically, though not necessarily, persistent and volatile memories are formed by physically distinct units (not shown). In addition, the memory may separately comprise plug-in memory such as a microSD card, and also subscriber information data on a subscriber information module (SIM) (not shown).

The smart phone 400 may also comprise a graphics processing unit (GPU) 416. The GPU 416 may communicate directly with the CPU 410 or via the I/O bridge, or may be part of the CPU 410. The GPU 416 may share RAM with the CPU 410 or may have its own dedicated RAM (not shown) and is connected to the display 418 of the mobile phone 400. The display 418 is typically a liquid crystal (LCD) or organic light-emitting diode (OLED) display, but may be any suitable display technology, such as e-ink. Optionally the GPU 416 may also be used to drive one or more loudspeakers 420 of the smart phone 400.

Alternatively, the speaker 420 may be connected to the CPU 410 via the I/O bridge 414 and the bus 430. Other components of the smart phone 400 may be similarly connected via the bus 430, including a touch surface 432 such as a capacitive touch surface overlaid on the screen 418 for the purposes of providing a touch input to the device, a microphone 434 for receiving speech from the user, one or more cameras 436 for capturing images, a global positioning system (GPS) unit 438 for obtaining an estimate of the smart phone's geographical position, and wireless communication means 440 (i.e. a transceiver).

The wireless communication means 440 may in turn comprise several separate wireless communication systems adhering to different standards and/or protocols, such as Bluetooth® (standard or low-energy variants), near field communication and Wi-Fi® as described previously, and also phone based communication such as 2G, 3G and/or 4G.

The systems are typically powered by a battery (not shown) that may be chargeable via a power input (not shown) that in turn may be part of a data link such as USB (not shown).

It will be appreciated that different smart phones 400 may include different features (for example a compass or a buzzer) and may omit some of those listed above (for example a touch surface).

Thus more generally, in an embodiment of the present disclosure a computing device such as smart phone 400 may comprise a CPU and a memory for storing and running an app to provide functionality in accordance with the principles described herein.

Accordingly, as described above and schematically represented in FIG. 4, in accordance with certain embodiments of the disclosure a system is provided which comprises an electronic aerosol provision device (e.g. an e-cigarette) for selectively providing an aerosol to a user of the electronic aerosol provision device, a biometric sensor (e.g. a heart rate monitor) for measure a biometric parameter (e.g. a heart rate) of the user of the electronic aerosol provision device, and a computing device (e.g. a smartphone) configured to communicate with the electronic aerosol provision device and the biometric sensor.

The computing device may run a software program (i.e. an application or "app") to configure the computing device to communicate with the electronic aerosol provision device to exchange operating data associated with the operation of the electronic aerosol provision device. The operating data relating to the aerosol provision device may comprise, for example, usage statistics transferred from the aerosol provision device to the computing device relating to the use of the aerosol provision device. This usage data may be presented to a user through a user interface of the app running on the computing device. Alternatively, or in addition, the operating data may comprise control (configuration) information transferred from the computing device to the aerosol provision device to control an aspect of the operation of the aerosol provision device. For example the control information may be arranged to modify an operational settings for the aerosol provision device, for example a power supply level for a heater of the aerosol device. Control information transferred to the aerosol the device from the computing device may be generated in response to user input through the user interface of the computing device and/or may be automatically generated by the computing device itself in response to particular conditions.

In accordance with certain embodiments of the disclosure, the software program/app running on the computing device that configures the computing device to support communications with the electronic aerosol provision device also configures the computing device to support communications with the biometric sensor, and in particular to allow the computing device to receive and process sensor data from the biometric sensor comprising an indication of one or more measurements of one or more biometric parameters of a user of the electronic aerosol provision device. The computing device in this example is further configured to control an aspect of its operation, and in particular an aspect of its operation relating to the electronic aerosol provision device, in response to the sensor data received from the biometric sensor.

Figure 7:
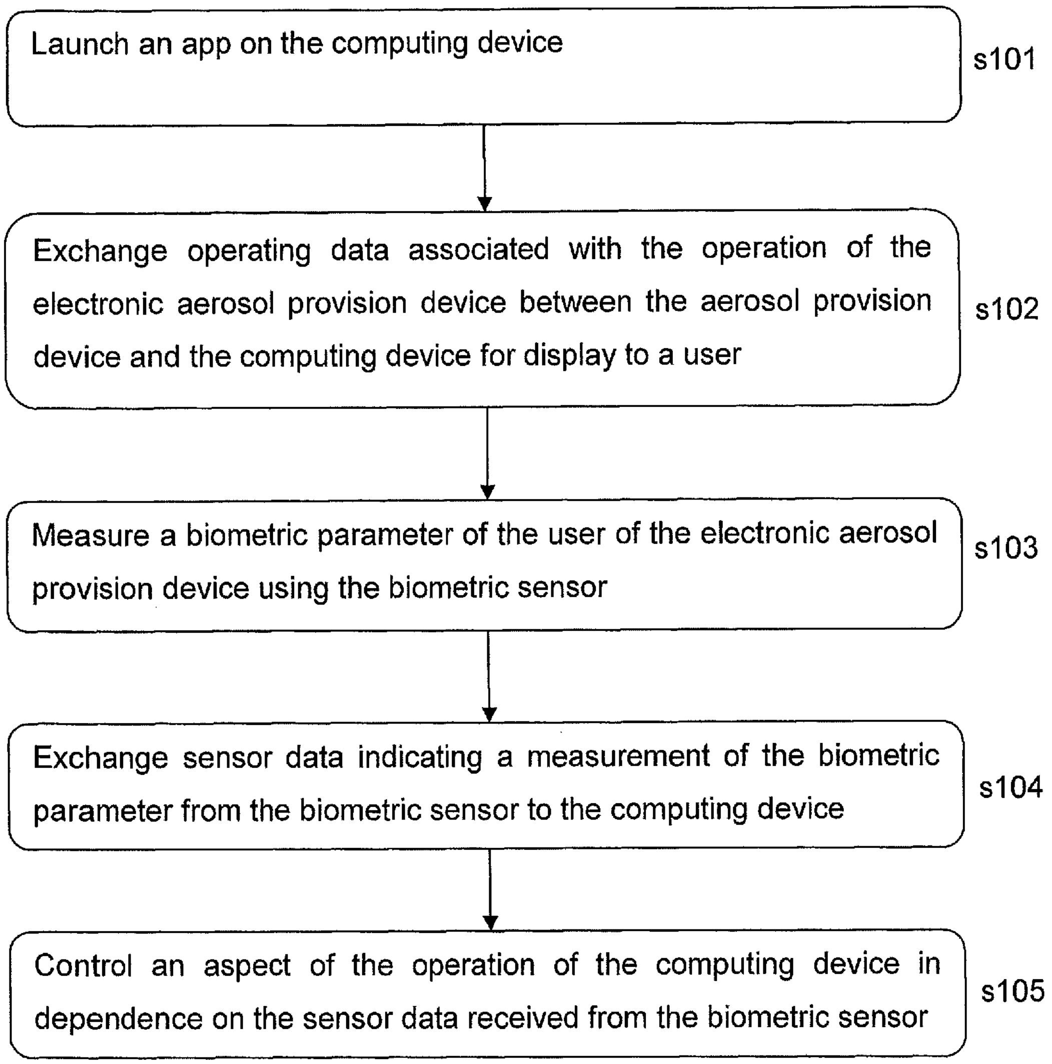
FIG. 7 is a flow diagram schematically representing a method of operating a system in accordance with an embodiment of the disclosure.

FIG. 7 is a flow diagram schematically showing a method of operating the system 600 schematically represented in FIG. 4 in accordance with an embodiment of the disclosure.

At S101 a software application (app) relating to the electronic aerosol provision device is launched on the computing device. This app may be provided by the manufacturer/vendor of the electronic aerosol provision device, or may be provided independently by another party. The app may provide a range of functionality associated with/relating to the electronic aerosol provision device, for example including functionality of the kind provided with known apps relating to electronic aerosol provision devices. Thus, the app may in some implementations cause the computing device to provide a user interface through which a user can view operating data associated with the aerosol provision device, for example frequency and times of use over a previous time period, as well as status information for the aerosol provision device, for example a battery level or power setting. The app may also allow the user to control one or more operational aspects of the electronic aerosol provision device, for example setting a nominal power level for a heater of the device, through the user interface provided by the computing device. It will be appreciated the app may be written/created to provide the functionality described herein using conventional programming techniques.

At S102 of the example represented in FIG. 7, operating data associated with the operation of the electronic aerosol provision device is communicated from the electronic aerosol provision device to the computing device for display to the user through the user interface provided by the app running on the computing device. As noted above, this operating data may, for example, comprise an indication of previous usage and or status information relating to the electronic aerosol provision device.

At S103 the biometric sensor measures a biometric parameter, e.g. heart rate, of the user of the electronic aerosol provision device. As noted above, this may be performed in accordance with conventional biometric sensing techniques.

At S104 the biometric sensor communicates sensor data to the computing device which indicates a measurement of the relevant biometric parameter. As will be appreciated, the communication and data coding protocols associated with the transfer of information between the various elements of the system may be performed in accordance with established wireless communication techniques.

At S105, after having received the indication of the measurement of the biometric parameter from the biometric sensor, the computing device is configured to control an aspect of its operation relating to the electronic aerosol provision device in response to the sensor data.

There are various different ways in which the computing device may control an aspect of its operation in response to the sensor data.

For example, in one implementation the step of the computing device controlling an aspect of its operation may involve the computing device updating a user interface to provide a user with information relating to the measurement of the biometric parameter associated with the sensor data, i.e. to provide a user with feedback relating to the biometric measurement(s). For example, the computing device may be configured to include an indication of the measurement of a relevant biometric parameter within through the user interface presented to the user in association with the aerosol provision device. Thus, a user may observe any effect the use of the electronic aerosol provision device has on the relevant biometric parameter. This may be of general interest to the user, and may furthermore allow the user to take account of the measurement of the biometric parameter in deciding how to proceed with using the electronic aerosol provision device. For example, if the user notes the sensor data provides an indication of an elevated heart rate, the user may elect to limit their use of the aerosol system for a period of time. This may be done by the user ceasing use or reducing an amount of aerosol generated by the aerosol provision device during use, for example by limiting the power supply to a heater of the aerosol provision device. In this regard the control may be provided through user input through the user interface of the computing device. In some example implementations the computing device may be configured to present the user with a value directly corresponding to the measurement of the biometric parameter, for example a value of the user's heart rate in terms of beats per minute. In another implementation, instead of, or in addition, to providing a specific value, the computing device may be configured to present the user, through the user interface, with an indication as to whether the biometric parameter falls within a particular predefined range, for example a preferred range or a less preferred range. It will be appreciated that what comprises a preferred range or and a less preferred range may be based on established medical opinions for the relevant biometric parameter. Thus, for example, if the sensor data from the biometric sensor indicates the user's heart rate is outside a predefined preferred range, an indication may be raised in the user interface. The indication may be provided in many ways, for example by sounding an audible signal or modifying the appearance of the display, for example changing the color or including a specific logo.

In another implementation the computing device may be configured to communicate an indication of the sensor data/biometric parameter measurement(s) to the electronic aerosol provision device, thereby allowing the electronic aerosol provision device to control its operation in dependence on the sensor data. For example, the aerosol provision device may include an indicator, for example a light emitting diode, which may be used to provide an indication of whether or not the sensor data indicate the relevant biometric parameter is within or without a predefined range (i.e. a range defined by two end points or defined by greater than or less than an individual value).

In another implementation the computing device may be configured to control the operation of the electronic aerosol provision device based on the sensor data. For example, the app may configure the computing device to compare a measurement of the biometric parameter with a predefined range of what is considered to be a preferred reading for the relevant parameter, for example based on established medical opinion. If the sensor data indicates the biometric parameter measurement falls outside the preferred range, the computing device may communicate control data to the aerosol provision device to modify the operation of the aerosol provision device, for example by providing instructions to stop or restrict the generation of aerosol by the aerosol provision device for a period of time. This may be achieved, for example, by stopping or reducing the amount of electrical power supplied to a heater of the aerosol provision device to generate the aerosol from an aerosol forming substrate/aerosol precursor material.

The system may be arranged so the biometric sensor 800 provides sensor data to the computing device representing measurements of the biometric parameter in accordance with a predefined schedule and/or may be configured so the biometric sensor communicates sensor data to the computing device in response to a request received from the computing device. Thus, the computing device may be configured to receive operating data from the electronic aerosol provision device indicating the electronic aerosol provision device has been used to generate vapor for a user, and may in response to this communicate with the biometric sensor 800 to request sensor data indicating a measurement of the biometric parameter.

It will be appreciated there are many different approaches and modifications that can be made in accordance with the general principle set out above in accordance with different embodiments of the disclosure.

For example, it will be appreciated that measurements of the biometric parameter by the biometric sensor may comprise one off individual measurements, or may comprise measurements derived from a number of individual measurements, for example, the sensor data may comprise an indication of a measurement which is an average, a minimum or a maximum, or some other statistically derived parameter, for a plurality of individual measurements of the biometric parameter made by the biometric sensor.

It will further be appreciated that whilst the above-described example has focused on the measurement of heart rate, similar principles can be applied in respect of other biometric parameters, for example in respect of any measurable aspect of a user which has the potential for change during periods of use of the electronic aerosol provision device.

It will further be appreciated that whilst the above-described example has focused on an implementation in which the electronic aerosol provision device, the computing device, and the biometric sensor comprise discrete components in wireless communication, in accordance with other example implementations, two or more of these components may be consolidated into a single device. For example, an electronic aerosol provision device and a biometric sensor may be combined into a single device, for example by providing a biometric sensor for measuring a user's heartbeat within a part of the aerosol provision device which the user will typically contact, for example a main body of the aerosol provision device which will typically be held by a user, or a mouthpiece which will typically be placed into contact with a user's lips during use. However, in practice it may be more likely for the biometric sensor to comprise a separate device from the electronic aerosol provision system because such biometric sensors are already widely available and in use, for example in "keep-fit" watches.

Furthermore, some or all of the functionality of the computing device in the example implementation discussed above may itself be provided by the electronic cigarette in accordance with some implementations.

Thus, there has been described a system comprising an electronic aerosol provision device for selectively providing an aerosol to a user of the electronic aerosol provision device, a computing device configured to communicate with the electronic aerosol provision device to exchange operating data associated with the operation of the electronic aerosol provision device, and a biometric sensor configured to measure a biometric parameter of the user of the electronic aerosol provision device and to communicate with the computing device to exchange sensor data indicating a measurement of the biometric parameter. The computing device is further configured to control an aspect of its operation relating to the electronic aerosol provision device in response to the sensor data received from the biometric sensor.

It will be appreciated that the above methods may be carried out on conventional hardware suitably adapted as applicable by software instruction or by the inclusion or substitution of dedicated hardware.

Thus the required adaptation to existing parts of an otherwise conventional equivalent device may be implemented in the form of a computer program product comprising processor implementable instructions stored on a tangible non-transitory machine-readable medium such as a floppy disk, optical disk, hard disk, PROM, RAM, flash memory or any combination of these or other storage media, or realized in hardware as an ASIC (application specific integrated circuit) or an FPGA (field programmable gate array) or other configurable circuit suitable to use in adapting the conventional equivalent device. Separately, such a computer program may be transmitted via data signals on a network such as an Ethernet, a wireless network, the Internet, or any combination of these of other networks.

Furthermore, while the above described embodiments have in some respects focused on some specific example aerosol provision devices, it will be appreciated the same principles can be applied for aerosol provision devices using other technologies. That is to say, the specific manner in which various aspects of the aerosol provision device function are not directly relevant to the principles underlying the examples described herein.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention (s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. An electronic aerosol provision system comprising:

an electronic cigarette for selectively providing an aerosol to a user of the electronic cigarette, wherein, when the user inhales on a mouthpiece, air is drawn into the electronic cigarette through one or more inlet holes, the air passing into a vaporizer where the air combines with vaporized aerosol forming substrate and then passes out of the mouthpiece to be inhaled by the user;

a computing device with a communications interface configured to communicate with the electronic cigarette to exchange operating data associated with operation of the electronic cigarette; and a biometric sensor comprising a transceiver unit, the biometric sensor separated from the electronic cigarette in use and configured to measure a biometric parameter of the user of the electronic cigarette and to communicate with the computing device using the transceiver unit to exchange sensor data indicating a measurement of the biometric parameter, the biometric parameter being a measurable aspect of the user which has the potential for change during periods of use of the electronic cigarette;

and wherein the computing device is configured to control an aspect of operation of the computing device relating to the electronic cigarette in response to the sensor data received from the biometric sensor, and wherein the computing device is configured to support wireless communications with the electronic cigarette and with the biometric sensor, wherein the computing device is configured to control the aspect of operation of the computing device relating to the electronic cigarette in response to the sensor data by providing operating data to the electronic cigarette that comprises control information for controlling an aspect of the operation of the electronic cigarette.

2. The electronic aerosol provision system of claim 1, wherein the computing device is configured to control the aspect of operation of the computing device relating to the electronic cigarette in response to the sensor data by updating a user interface providing the user of the electronic cigarette with information relating to the operation of the electronic cigarette to include an indication of the sensor data.

3. The electronic aerosol provision system of claim 2, wherein the indication of the sensor data included in the user interface comprises an indication of the measurement of the biometric parameter.

4. The electronic aerosol provision system of claim 2, wherein the indication of the sensor data included in the user interface comprises an indication of whether or not the measurement of the biometric parameter falls with a predefined range.

5. The electronic aerosol provision system of claim 1, wherein controlling the aspect of the operation of the electronic cigarette comprises configuring an indicator of the electronic cigarette to provide an indication relating to the sensor data.

6. The electronic aerosol provision system of claim 1, wherein controlling the aspect of the operation of the electronic cigarette comprises restricting an ability of the electronic cigarette to provide aerosol to the user.

7. The electronic aerosol provision system of claim 6, wherein the electronic cigarette comprises a heater for heating an aerosol precursor material to provide an aerosol to the user, and wherein restricting the ability of the electronic cigarette to provide aerosol to the user comprises preventing or limiting a supply of power to the heater for a period of time.

8. The electronic aerosol provision system of claim 1, wherein the computing device is configured to communicate with the biometric sensor to request sensor data from the biometric sensor in response to receiving operating data from the electronic cigarette comprising use data indicating that the electronic cigarette has been used to provide aerosol to the user.

9. The electronic aerosol provision system of claim 1, wherein the biometric sensor is selected from the group consisting of: a heart rate sensor for measuring a heart rate of the user, a blood pressure sensor for measuring a blood pressure of the user, a breathing rate sensor for measuring a breathing rate of the user, and a user activity sensor for measuring an aspect of an activity of the user.

10. An electronic cigarette for selectively providing an aerosol to a user of the electronic cigarette, wherein, when the user inhales on a mouthpiece, air is drawn into the electronic cigarette through one or more inlet holes, the air passing into a vaporizer where the air combines with a vaporized aerosol forming substrate and then passes out of the mouthpiece to be inhaled by the user, the electronic cigarette comprising:

a communications interface configured to communicate with a computing device to exchange operating data associated with operation of the electronic cigarette, wherein the computing device is configured to control an aspect of operation of the computing device relating to the electronic cigarette in response to sensor data received from a biometric sensor comprising a transceiver unit, the biometric sensor separated from the electronic cigarette in use and configured to measure a biometric parameter of the user of the electronic cigarette and to communicate with the computing device using the transceiver unit to exchange the sensor data indicating a measurement of the biometric parameter, the biometric parameter being a measurable aspect of the user which has the potential for change during periods of use of the electronic cigarette, wherein the computing device is configured to support wireless communications with the electronic cigarette and with the biometric sensor, wherein the computing device is configured to control the aspect of operation of the computing device relating to the electronic cigarette in response to the sensor data by providing operating data to the electronic cigarette that comprises control information for controlling an aspect of the operation of the electronic cigarette.

11. A method of operating an electronic aerosol provision system comprising an electronic cigarette, a computing device with a communications interface configured to communicate with the electronic cigarette to exchange operating data associated with operation of the electronic cigarette, and a biometric sensor comprising a transceiver unit, the biometric sensor separated from the electronic cigarette in use and configured to measure a biometric parameter of a user of the electronic cigarette and to communicate with the computing device using the transceiver unit to exchange sensor data indicating a measurement of the biometric parameter, wherein, when the user inhales on a mouthpiece of the electronic cigarette, air is drawn into the electronic cigarette through one or more inlet holes, the air passing into a vaporizer where the air combines with a vaporized aerosol forming substrate and then passes out of the mouthpiece to be inhaled by the user, and wherein the computing device is configured to support wireless communications with the electronic cigarette and with the biometric sensor, wherein the method comprises:

the biometric sensor measuring a biometric parameter of the user of the electronic cigarette and communicating sensor data indicating a measurement of the biometric parameter to the computing device, the biometric parameter being a measurable aspect of the user which has the potential for change during periods of use of the electronic cigarette; and the computing device controlling an aspect of operation of the computing device relating to the electronic cigarette in response to the sensor data received from the biometric sensor, wherein the computing device is configured to control the aspect of operation of the computing device relating to the electronic cigarette in response to the sensor data by providing operating data to the electronic cigarette that comprises control information for controlling an aspect of the operation of the electronic cigarette.

12. A computing device configured to communicate with an electronic cigarette, wherein, when a user inhales on a mouthpiece, air is drawn into the electronic cigarette through one or more inlet holes, the air passing into a vaporizer where the air combines with a vaporized aerosol forming substrate and then passes out of the mouthpiece to be inhaled by the user, the computing device configured to exchange operating data associated with operation of the electronic cigarette and to communicate with a biometric sensor comprising a transceiver unit by using the transceiver unit, the biometric sensor separated from the electronic cigarette in use to receive sensor data from the biometric sensor indicating a measurement of a biometric parameter of the user of the electronic cigarette, the biometric parameter being a measurable aspect of the user which has the potential for change during periods of use of the electronic cigarette, wherein the computing device comprises:

a processor configured to control an aspect of operation of the computing device relating to the electronic cigarette in response to the sensor data received from the biometric sensor, wherein the computing device is configured to support wireless communications with the electronic cigarette and with the biometric sensor, wherein the processor is configured to control the aspect of operation of the computing device relating to the electronic cigarette in response to the sensor data by providing operating data to the electronic cigarette that comprises control information for controlling an aspect of the operation of the electronic cigarette.

13. A method of operating a computing device configured to communicate with an electronic cigarette to exchange operating data associated with the operation of the electronic cigarette, wherein when a user inhales on a mouthpiece, air is drawn into the electronic cigarette through one or more inlet holes, the air passing into a vaporizer where the air combines with a vaporized aerosol forming substrate and then passes out of the mouthpiece to be inhaled by the user, the method comprising:

communicating with a biometric sensor comprising a transceiver unit by using the transceiver unit, the biometric sensor separated from the electronic cigarette in use to receive sensor data from the biometric sensor indicating a measurement of a biometric parameter of the user of the electronic cigarette, the biometric parameter being a measurable aspect of the user which has the potential for change during periods of use of the electronic cigarette; and controlling an aspect of operation of the computing device relating to the electronic cigarette in response to the sensor data received from the biometric sensor, wherein the computing device is configured to support wireless communications with the electronic cigarette and with the biometric sensor, wherein the computing device is configured to control the aspect of operation of the computing device relating to the electronic cigarette in response to the sensor data by providing operating data to the electronic cigarette that comprises control information for controlling an aspect of the operation of the electronic cigarette.

14. A non-transitory computer-readable storage element storing a computer program product comprising machine readable instructions which, when executed on a computing device, configure the computing device to:

communicate, wirelessly, with an electronic cigarette to exchange operating data associated with the operation of the electronic cigarette, wherein when a user inhales on a mouthpiece, air is drawn into the electronic cigarette through one or more inlet holes, the air passing into a vaporizer where the air combines with a vaporized aerosol forming substrate and then passes out of the mouthpiece to be inhaled by the user;

communicate, wirelessly, with a biometric sensor comprising a transceiver unit by using the transceiver unit, the biometric sensor separated from the electronic cigarette in use to receive sensor data from the biometric sensor indicating a measurement of a biometric parameter of the user of the electronic cigarette, the biometric parameter being a measurable aspect of the user which has the potential for change during periods of use of the electronic cigarette, and control an aspect of operation of the computing device relating to the electronic cigarette in response to the sensor data received from the biometric sensor, wherein the computing device is configured to control the aspect of operation of the computing device relating to the electronic cigarette in response to the sensor data by providing operating data to the electronic cigarette that comprises control information for controlling an aspect of the operation of the electronic cigarette.

15. An electronic aerosol provision system comprising:

electronic aerosol provision means for selectively providing an aerosol to a user of the electronic aerosol provision means wherein, when the user inhales on a mouthpiece, air is drawn into the electronic aerosol provision means through one or more inlet holes, the air passing into a vaporizer where the air combines with a vaporized aerosol forming substrate and then passes out of the mouthpiece to be inhaled by the user;

computing means for communicating with the electronic aerosol provision means to exchange operating data associated with operation of the electronic aerosol provision means; and biometric sensor means comprising a transceiver unit, the biometric sensor means separated from the electronic aerosol provision means in use and for measuring a biometric parameter of the user of the electronic aerosol provision means and communicating with the computing means using the transceiver unit to exchange sensor data indicating a measurement of the biometric parameter, the biometric parameter being a measurable aspect of the user which has the potential for change during periods of use of the electronic aerosol provision means;

and wherein the computing means controls an aspect of operation of the computing means relating to the electronic aerosol provision means in response to the sensor data received from the biometric sensor means, wherein the computing means is configured to support wireless communications with the electronic aerosol provision means and with the biometric sensor means, wherein the computing means is configured to control the aspect of operation of the computing means relating to the electronic aerosol provision means in response to the sensor data by providing operating data to the electronic aerosol provision means that comprises control information for controlling an aspect of the operation of the electronic aerosol provision means.

* * * * *